US012766042B2

(12) United States Patent
Biggs

(10) Patent No.: US 12,766,042 B2
(45) Date of Patent: Oct. 20, 2026

(54) COMPRESSION PANTS FOR LIPEDEMA

(71) Applicant: Glenda Biggs, Lloydminster (CA)

(72) Inventor: Glenda Biggs, Lloydminster (CA)

( * ) Notice: Subject to any disclaimer, the term of this patent is extended or adjusted under 35 U.S.C. 154(b) by 0 days.

(21) Appl. No.: 18/816,844

(22) Filed: Aug. 27, 2024

(65) Prior Publication Data

US 2025/0073086 A1 Mar. 6, 2025

(30) Foreign Application Priority Data

Sep. 1, 2023 (CA) ................................ CA 3210936

(51) Int. Cl.
*A61F 13/00* (2024.01)
*A61F 13/06* (2006.01)

(52) U.S. Cl.
CPC .................................... *A61F 13/06* (2013.01)

(58) Field of Classification Search
None
See application file for complete search history.

(56) References Cited

U.S. PATENT DOCUMENTS 7,945,970 B2 5/2011 Belluye et al.
D646,047 S 10/2011 Arensdorf
8,784,351 B2 7/2014 Dumpson et al.
9,402,779 B2 8/2016 Brown et al.
2006/0085894 A1 4/2006 Yakopson et al.
2007/0033696 A1 2/2007 Sellier
2009/0113596 A1 5/2009 Young
2011/0208104 A1* 8/2011 Sellier .................... A61H 7/001 2/69
2014/0283281 A1* 9/2014 Willis ................ A41D 13/0058 2/228
2015/0196070 A1* 7/2015 Burger ............... A41D 13/0506 2/465
2017/0360619 A1 12/2017 Al-Arab
2020/0288797 A1* 9/2020 Krysinski ............... A61F 13/08

FOREIGN PATENT DOCUMENTS

CN 103462248 B 1/2015
DE 102004022504 A1 * 6/2005 ............. A61F 13/06
EP 1 802 208 B1 8/2016
EP 3257487 A1 * 12/2017 ........... A61F 13/085
KR 10-1987964 B1 6/2019
WO WO 96/08174 * 3/1996

(Continued)

OTHER PUBLICATIONS

DE 102001022504 Translation (Year: 2005).*
EP 3057487 Translation (Year: 2017).*

*Primary Examiner* — Kim M Lewis
(74) *Attorney, Agent, or Firm* — The Marbury Law Group, PLLC

(57) ABSTRACT

Compression pants for lipedema include a lower waist portion, a hip portion, a right thigh portion and a left thigh portion. The hip portion is positioned below and depends from the lower waist portion. The hip portion is larger than the lower waist portion. The right thigh portion and the left thigh portion are positioned below and depend from the lower waist portion. Each of the right thigh portion and the left thigh portion have an upper part and a lower part. The upper part is larger in circumference than the lower part and the upper part tapers in size into the lower part.

16 Claims, 9 Drawing Sheets

(56) References Cited

FOREIGN PATENT DOCUMENTS

| | | | | |
|---|---|---|---|---|
| WO | 01/00118 | A1 | | 1/2001 |
| WO | WO 2014/114925 | A1 | * | 7/2014 |
| WO | 2022/144478 | A1 | | 7/2022 |
| WO | 02/064073 | A1 | | 8/2022 |
| WO | WO 2022/253440 | A1 | * | 12/2022 |

* cited by examiner

COMPRESSION PANTS FOR LIPEDEMA

FIELD OF THE DISCLOSURE

The present application relates generally to compression garments for patients with lipedema, and more specifically relates to compression pants for patients with lipedema.

BACKGROUND

This section provides background information to facilitate a better understanding of the various aspects of the invention. It should be understood that the statements in this section of this document are to be read in this light, and not as admissions of prior art.

Lipedema is a chronic condition that affects about 10% of the female population and symptoms often begin at puberty. The condition results in the buildup of disproportionate fat and connective tissues in legs and hips. Disproportionate fat is observed when fat accumulates in a non-uniform manner throughout a limb. This is different from obesity where fat deposits tend to accumulate in a more uniform manner, in other words, the entire limb of an obese person is larger whereas a person suffering from lipedema will have portions of their limb be larger while other portions appear more "normal". Arms may also be affected. Lipedema can be painful and as it progresses can cause issues with proper lymphatic draining which can further exacerbate the issue by causing additional swelling. Unlike obesity, which results in relatively proportionate fat building throughout the body, lipedema fat grows while the rest of the body stays the same. Lipedema is not caused by overeating and it is believed that genetics play a role in developing lipedema. With no known cure, it is only possible to treat the symptoms associated with this condition.

There are five different types of lipedema, four related to the lower body and one related to the upper body. The different types can require different types of compression or compression in different areas to provide relief. Type 1 affects below the bellybutton, the hips, and the buttocks. Type 2 affects below the bellybutton to the knees. Type 3 affects below the bellybutton to the ankles. Type 4 affects the arms. Type 5 affects the lower legs. While compression can help in treating lipedema, currently the only real solution for sufferers is to purchase expensive custom made garments.

BRIEF SUMMARY

There is provided a compression pants for lipedema that has a lower waist portion, a hip portion, a right thigh portion and a left thigh portion. The hip portion is positioned below and depending from the lower waist portion. The hip portion is larger than the lower waist portion. The right thigh portion and the left thigh portion are positioned below and depending from the waist portion. Each of the right thigh portion and the left thigh portion have an upper part and a lower part. The upper part is larger in circumference than the lower part, and the upper part tapers in size into the lower part.

In one embodiment, an upper waist portion is provided and is positioned above and depending from the lower waist portion.

In one embodiment, there is also provided a right lower leg portion and a left lower leg portion. The right lower leg portion depends from the lower part of the right thigh portion and the left lower leg portion depends from the lower part of the left thigh portion. Each of the right lower leg portion and the left lower leg portion have a knee portion, a calf portion, and an ankle portion. The calf portion is smaller in circumference than the lower part of the right thigh portion and the left thigh portion. The ankle portion is smaller in circumference than the calf portion.

In one embodiment, there is also provided a foot portion that depends from the ankle portion. The foot portion extends from the ankle portion towards a wearer's toes.

In one embodiment, the lower waist portion is 25% smaller to 5% larger in circumference than the hip portion. Each of the upper part of the right thigh portion and the upper part of the left thigh portion are 30-45% smaller in circumference than the hip portion. Each of the lower part of the right thigh portion and the lower part of the left thigh portion are 50-60% smaller in circumference than the hip portion.

In one embodiment, the calf portion is 55-75% smaller in circumference than the hip portion and the ankle portion is 70-85% smaller in circumference than the hip portion.

In one embodiment, the calf portion is 60-70% smaller in circumference than the hip portion and the ankle portion is 70-85% smaller in circumference than the hip portion.

In one embodiment, the calf portion is 50-60% smaller in circumference than the hip portion and the ankle portion is 70-80% smaller in circumference than the hip portion.

In one embodiment, the left thigh portion and the left lower leg portion accommodate a combined left leg volume of at least 9000 mL and the right thigh portion and the right lower leg portion accommodate a combined right leg volume of at least 9000 mL.

In one embodiment, a foam pad is positioned at a predetermined location of the compression pats for lipedema. Predetermined locations may include a side of the wearer's knee, a side of the wearer's hip, or any other suitable location where different pressure being applied may result in some comfort to the wearer.

In one embodiment, the foam pad has a contacting surface that is positioned such that it is adjacent a wearer's body. The contacting surface has at least one lymph channel.

In one embodiment, a closure such as a zipper, Velcro, hooks, snaps, buttons, or ties may be positioned adjacent the predetermined location to facilitate insertion of the foam pad.

In one embodiment, a pad pocket may be provided at the predetermined location for holding the foam pad. This can help prevent the foam pad from moving out of position.

In one embodiment, the foam pad is held in position through compression of the compression pants for lipedema.

In one embodiment, a removable inner liner is positionable between the compression pants for lipedema and a wearer's lower leg. Removable liner may include a built in foam with channels to facilitate lymphatic flow, an absorption liner for collecting fluids, or a combination of both.

In one embodiment, at least a portion of the compression pants for lipedema are flat-knit.

In one embodiment, at least a portion of the compression pants for lipedema are circular-knit.

BRIEF DESCRIPTION OF THE DRAWINGS

These and other features will become more apparent from the following description in which references are made to the following drawings, in which numerical references denote like parts. The drawings are for the purpose of illustration only and are not intended to in any way limit the scope of the invention to the particular embodiments shown.

DETAILED DESCRIPTION OF THE PREFERRED EMBODIMENTS

Figure 1:
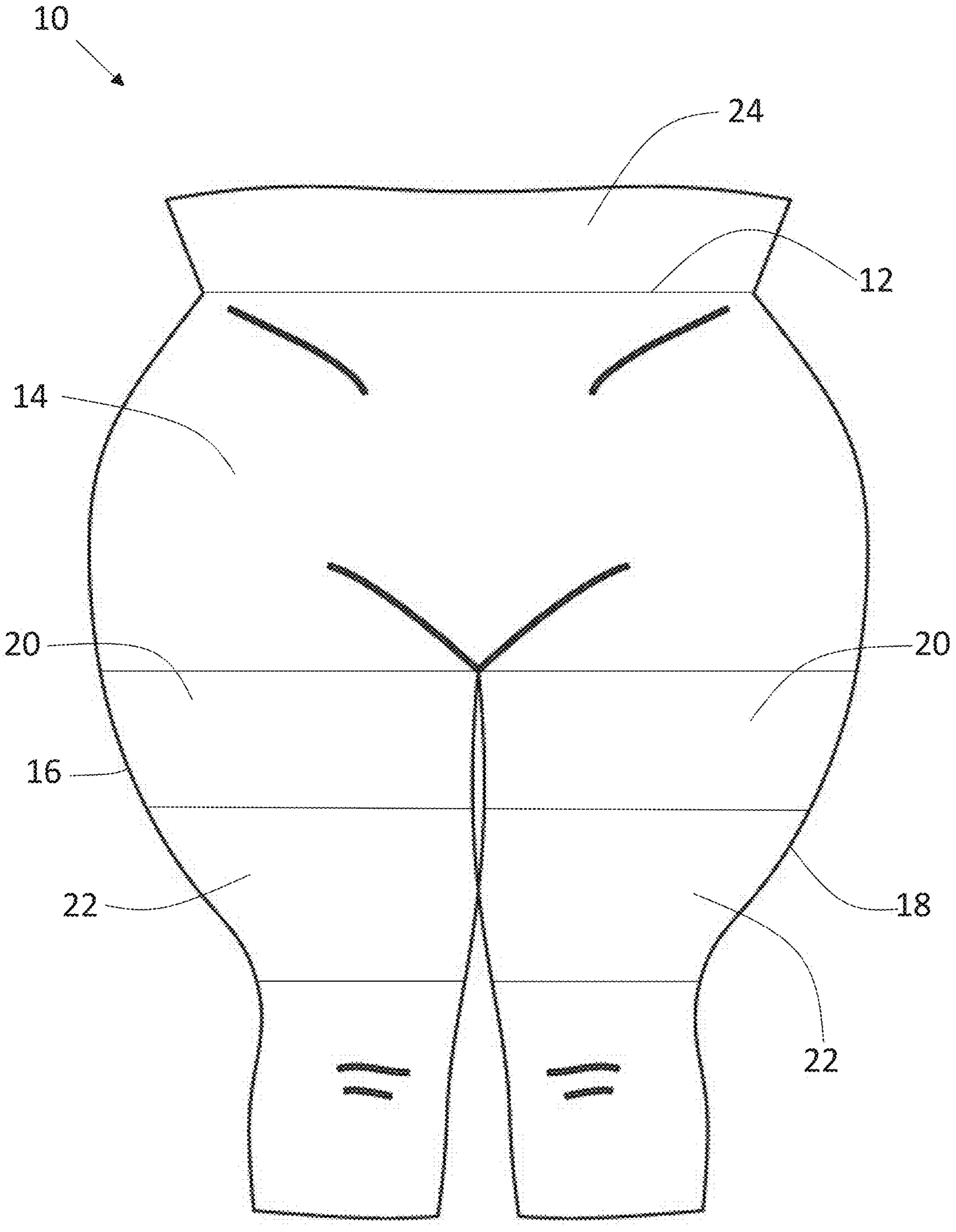
FIG. 1 is a front elevation view of compression pants for lipedema in capri form.

Compression pants for lipedema, generally identified by reference numeral 10, will now be described with reference to FIG. 1 through FIG. 13.

Referring to FIG. 1, compression pants for lipedema 10 has a lower waist portion 12, a hip portion 14, a right thigh portion 16 and a left thigh portion 18. Hip portion 14 is positioned below and depends from lower waist portion 12. Hip portion 14 is larger than lower waist portion 12. Right thigh portion 16 and left thigh portion 18 are positioned below and depend from lower waist portion 12. Each of right thigh portion 16 and left thigh portion 18 have an upper part 20 and a lower part 22. Upper part 22 is larger in circumference than lower part 22 and upper part 20 tapers in size into lower part 22. An upper waist portion 24 is provided that is positioned above and depending from lower waist portion 12. Upper waist portion 24 is beneficial as it can provide greater compression to a wearer's waist and hips when utilized. However, since not all wearers are able to tolerate the greater compression, upper waist portion 24 may not be desired in every case. In the embodiments shown in FIG. 1, compression pants for lipedema 10 is a capri style pants and may only provide compression from the wearer's waist to above the wearers knee. This style may be useful for treating lipedema types 1 and 2. The capri style may also be beneficial where custom compression is required on the lower leg or compression on the lower leg cannot be tolerated by the wearer.

Figure 2:
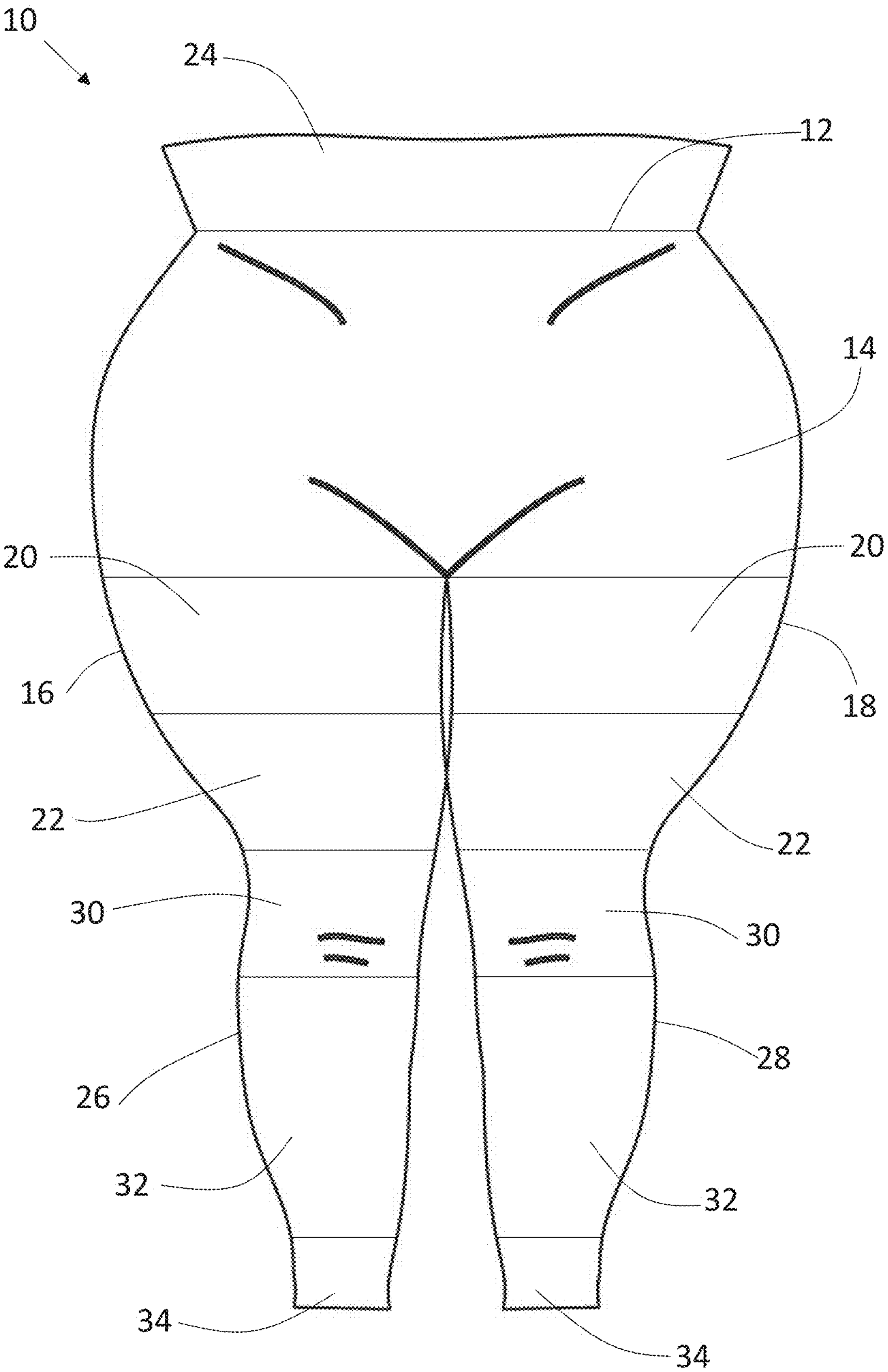
FIG. 2 is a front elevation view of compression pants for lipedema having a lower leg portion.
Figure 3:
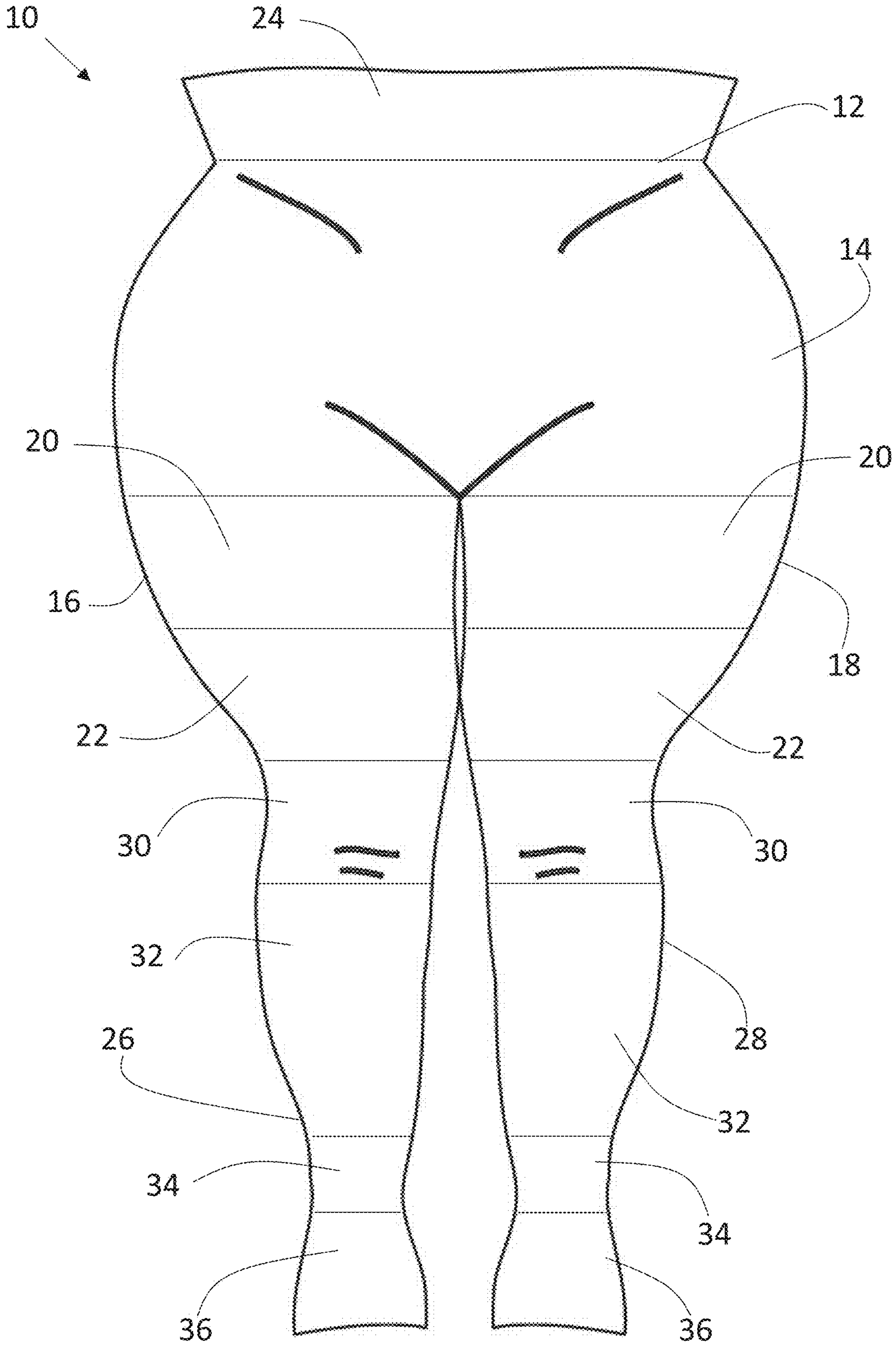
FIG. 3 is a front elevation view of compression pants for lipedema having a foot portion.

Referring to FIG. 2, a right lower leg portion 26 and a left lower leg portion 28. The right lower leg portion 26 depends from lower part 22 of right thigh portion 16 and left lower leg portion 28 depends from lower part 22 of left thigh portion 18. Each of the right lower leg portion 26 and the left lower leg portion 28 have a knee portion 30, a calf portion 32, and an ankle portion 34. Calf portion 32 is smaller in circumference than lower part 22 of right thigh portion 16 and left thigh portion 18. Ankle portion 34 is smaller in circumference than calf portion 32. Use of compression pants for lipedema 10 that can incorporate right lower leg portion 26 and left lower leg portion 28 may be beneficial in association with any of types 1, 2, 3, or 5 but most particularly for types 2, 3 and 5. Referring to FIG. 3, a foot portion 36 may depend from ankle portion 34 and extend from ankle portion 34 towards a wearer's toes. Foot portion 36 may provide compression for the ankle and into the foot and is most often beneficial for sufferers of types 3 and 5. Foot portion 36 generally covers ½ to ¾ of a wearer's foot, however it will be understood by a person skilled in the art that more or less of the foot may be covered.

Type 1 lipedema tends to affect under the bellybutton, the hip, and buttocks of the sufferer. While every individual suffering from lipedema is different, those suffering from type 1 generally have the same overall shape of their lower bodies. Compression pants for lipedema 10 that can be beneficial for individuals with type 1 are shaped such that lower waist portion 12 is 25% smaller to 5% larger in circumference than hip portion 14, upper part 20 of right thigh portion 16 and upper part 20 of left thigh portion 18 are each 30-45% smaller in circumference than hip portion 14, and lower part 22 of right thigh portion 16 and lower part 22 of left thigh portion 18 are each 50-60% smaller in circumference than hip portion 14. These proportions will allow many women with type 1 lipedema to fit comfortably into compression pants for lipedema 10. When upper waist portion 24 is present, it will have the same circumference or a slightly larger circumference than lower waste portion 12. When full length compression pants are worn, calf portion 32 is 55-75% smaller in circumference than hip portion 14 and ankle portion 34 is 70-85% smaller in circumference than hip portion 14. The circumference of compression pants for lipedema 10 will taper from lower part 22 of right thigh portion 16 and lower part 22 of left thigh portion 18 to calf portion 32 and ankle portion 34. Sufferers of type 1 lipedema generally start with "normal" sized lower legs since the abnormal fat deposits are found under the bellybutton, and on the hips and buttocks. It will be understood by a person skilled in the art that the circumference of the different portions of compression pants for lipedema is measurable based upon the stretchable nature of the compression materials used. For example, when compression pants for lipedema are stretched to provide a preferred compression, lower waist portion 12 is 25% smaller to 5% larger in circumference than hip portion 14. When unstretched, lower waist portion 12 may not appear to be 25% smaller to 5% larger in circumference when compared to the unstretched hip portion 14.

As an example only, a possible size chart for sufferers of type 1 lipedema is provided below with measurements in cm. If compression is too great for an individual at one size, sizing up may reduce the amount of compression. It will be understood by a person skilled in the art that these are not the only acceptable sizes or measurements that may be used:

| Size | A-1 | B-1 | C-1 | D-1 | E-1 | F-1 | G-1 | H-1 |
|---|---|---|---|---|---|---|---|---|
| Waist | 70-85 | 80-90 | 85-100 | 90-115 | 110-125 | 120-135 | 130-145 | 145-165 |
| Hip | 85-110 | 105-115 | 110-120 | 115-125 | 120-130 | 125-135 | 130-140 | 140-160 |
| Upper Thigh | 60-65 | 62-69 | 65-70 | 68-75 | 70-77 | 75-80 | 78-85 | 83-93 |
| Lower Thigh | 42-46 | 45-50 | 47-52 | 49-54 | 53-58 | 55-60 | 58-63 | 62-67 |
| Calf | 35-37 | 37-40 | 36-39 | 37-40 | 38-41 | 39-42 | 41-44 | 42-46 |
| Ankle | 21-25 | 21-25 | 21-25 | 22-26 | 22-26 | 22-26 | 22-26 | 22-26 |

Type 2 lipedema tends to affect under the bellybutton, the hip, buttocks, and thighs. In some cases, fat deposits at the knee may also exist in type 2. Compression pants for lipedema 10 that can be beneficial for individuals with type 2 are shaped such that lower waist portion 12 is 25% smaller to 5% larger in circumference than hip portion 14, upper part 20 of right thigh portion 16 and upper part of left thigh portion 18 are each 30-45% smaller in circumference than hip portion 14, and lower part 22 of right thigh portion 16 and lower part 22 of left thigh portion 18 are each 50-60% smaller in circumference than hip portion 14. These proportions will allow many women with type 2 lipedema to fit comfortably into compression pants for lipedema 10. When upper waist portion 24 is present, it will have the same circumference or a slightly larger circumference than lower waste portion 12. When full length compression pants are worn, calf portion 32 is 60-70% smaller in circumference than hip portion 14 and ankle portion 34 is 70-85% smaller in circumference than hip portion 14. The circumference of compression pants for lipedema 10 will taper from lower part 22 of right thigh portion 16 and lower part 22 of left thigh portion 18 to calf portion 32 and ankle portion 34. Sufferers of type 2 lipedema generally have "normal" sized lower legs since the abnormal fat deposits are found above the knee. It will be understood by a person skilled in the art that the circumference of the different portions of compression pants for lipedema is measurable based upon the stretchable nature of the compression materials used. For example, when compression pants for lipedema are stretched to provide a preferred compression, lower waist portion 12 is 25% smaller to 5% larger in circumference than hip portion 14. When unstretched, lower waist portion 12 may not appear to be 25% smaller to 5% larger in circumference when compared to the unstretched hip portion 14.

As an example only, a possible size chart for sufferers of type 2 lipedema is provided below with measurements in cm. If compression is too great for an individual at one size, sizing up may reduce the amount of compression. It will be understood by a person skilled in the art that these are not the only acceptable sizes or measurements that may be used:

| Size | A-1 | B-1 | C-1 | D-1 | E-1 | F-1 | G-1 | H-1 |
|---|---|---|---|---|---|---|---|---|
| Waist | 70-85 | 80-90 | 85-100 | 90-115 | 110-125 | 120-135 | 125-145 | 145-165 |
| Hip | 85-110 | 105-115 | 110-120 | 115-125 | 120-130 | 125-135 | 130-140 | 140-160 |
| Upper Thigh | 58-63 | 60-69 | 61-69 | 67-76 | 74-80 | 76-83 | 78-87 | 80-95 |
| Lower Thigh | 40-45 | 44-49 | 48-53 | 52-57 | 55-61 | 60-65 | 64-70 | 60-68 |
| Calf | 28-35 | 33-37 | 35-42 | 38-46 | 40-48 | 42-50 | 45-53 | 46-56 |
| Ankle | 22-25 | 22-25 | 22-25 | 24-26 | 24-26 | 25-27 | 26-29 | 26-29 |

Type 3 lipedema tends to affect the sufferer's entire lower body, from below the bellybutton to the ankles. Compression pants for lipedema 10 that can be beneficial for individuals with type 3 are shaped such that lower waist portion 12 is 25% smaller to 5% larger in circumference than hip portion 14, upper part 20 of right thigh portion 16 and upper part of left thigh portion 18 are each 30-45% smaller in circumference than hip portion 14, and lower part 22 of right thigh portion 16 and lower part 22 of left thigh portion 18 are each 50-60% smaller in circumference than hip portion 14. These proportions will allow many women with type 3 lipedema to fit comfortably into compression pants for lipedema 10. When upper waist portion 24 is present, it will have the same circumference or a slightly larger circumference than lower waste portion 12. When full length compression pants are worn, calf portion 32 is 50-60% smaller in circumference than hip portion 14 and ankle portion 34 is 70-80% smaller in circumference than hip portion 14. The circumference of compression pants for lipedema 10 will taper from lower part 22 of right thigh portion 16 and lower part 22 of left thigh portion 18 to calf portion 32 and ankle portion 34. It will be understood by a person skilled in the art that the circumference of the different portions of compression pants for lipedema is measurable based upon the stretchable nature of the compression materials used. For example, when compression pants for lipedema are stretched to provide a preferred compression, lower waist portion 12 is 25% smaller to 5% larger in circumference than hip portion 14. When unstretched, lower waist portion 12 may not appear to be 25% smaller to 5% larger in circumference when compared to the unstretched hip portion 14.

As an example only, a possible size chart for sufferers of type 3 lipedema is provided below with measurements in cm. If compression is too great for an individual at one size, sizing up may reduce the amount of compression. It will be understood by a person skilled in the art that these are not the only acceptable sizes or measurements that may be used:

| Size | A-1 | B-1 | C-1 | D-1 | E-1 | F-1 | G-1 | H-1 |
|---|---|---|---|---|---|---|---|---|
| Waist | 70-85 | 80-90 | 85-100 | 90-115 | 110-125 | 120-135 | 130-145 | 145-165 |
| Hip | 85-110 | 105-115 | 110-120 | 115-125 | 120-130 | 125-135 | 130-140 | 140-160 |
| Upper Thigh | 58-63 | 60-69 | 61-69 | 67-76 | 74-80 | 78-83 | 82-87 | 85-95 |
| Lower Thigh | 40-45 | 44-49 | 48-53 | 52-57 | 55-61 | 60-65 | 64-70 | 60-75 |
| Calf | 40-48 | 45-53 | 47-54 | 49-56 | 51-58 | 53-60 | 55-62 | 57-64 |
| Ankle | 22-30 | 23-31 | 23-31 | 24-32 | 24-32 | 26-34 | 27-37 | 28-38 |

Type 5 lipedema is unique in that it only affects the lower legs. Compression pants for lipedema 10 that can be beneficial for individuals with type 5 are shaped such that above the knee shapes are based off of sizing for "normal" pants and below the knee is sized such that calf portion 32 is 50-60% smaller in circumference than hip portion 14 and ankle portion 34 is 70-80% smaller in circumference than hip portion 14.

Regardless of whether an individual has type 1, 2, 3, or 5, compression pants for lipedema are sized to accommodate a left leg volume of at least 9000 mL and a right leg volume of at least 9000 mL. Left leg volume is calculated by calculating the sum of the volume of left thigh portion 18 and the volume of left lower leg portion 28. Right leg volume is calculated by calculating the sum of the volume of right thigh portion 16 and the volume of right lower leg portion 26. These calculations may be done manually or with the assistance of a computer measurement program.

Figure 4:
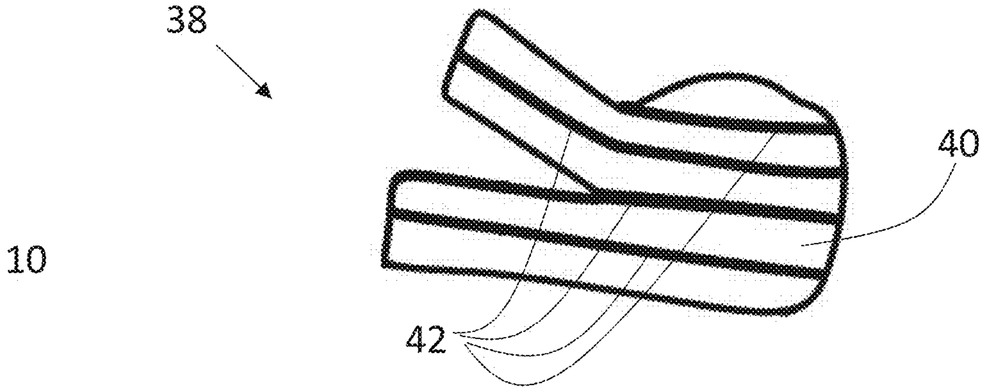
FIG. 4 is a front elevation view of a foam pad.
Figure 5:
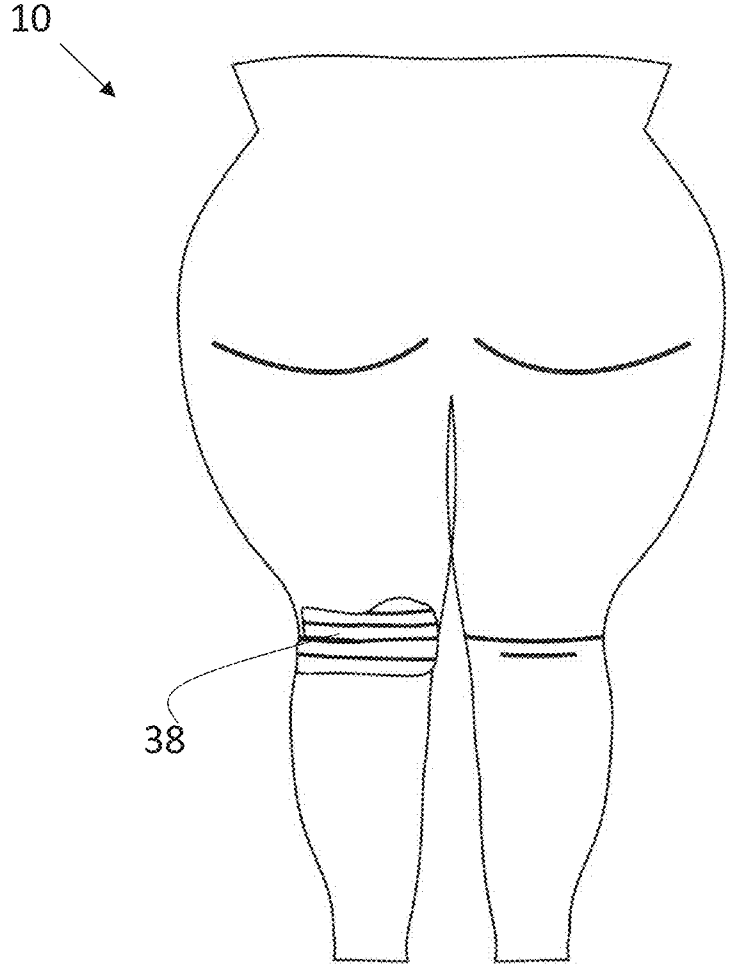
FIG. 5 is a rear elevation view of the foam pad positioned behind a wearer's knee.
Figure 6:
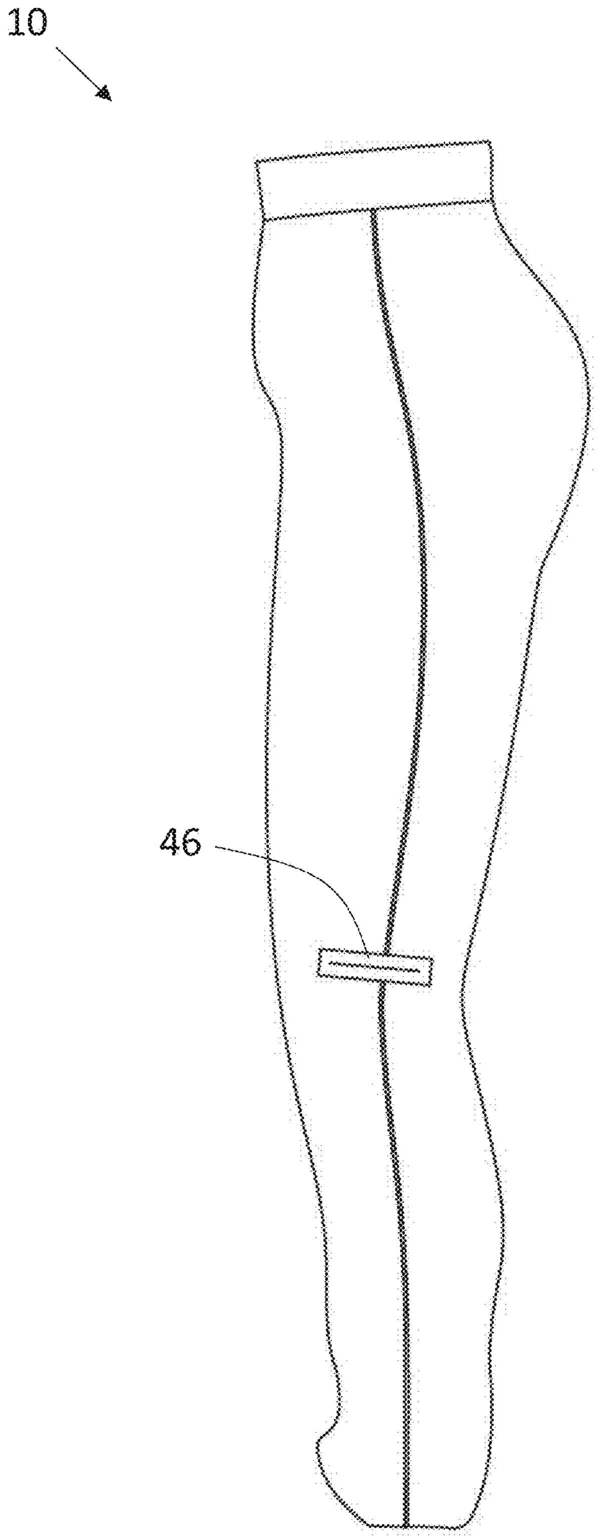
FIG. 6 is a side elevation view of the compression pants for lipedema with a pad pocket.
Figure 7:
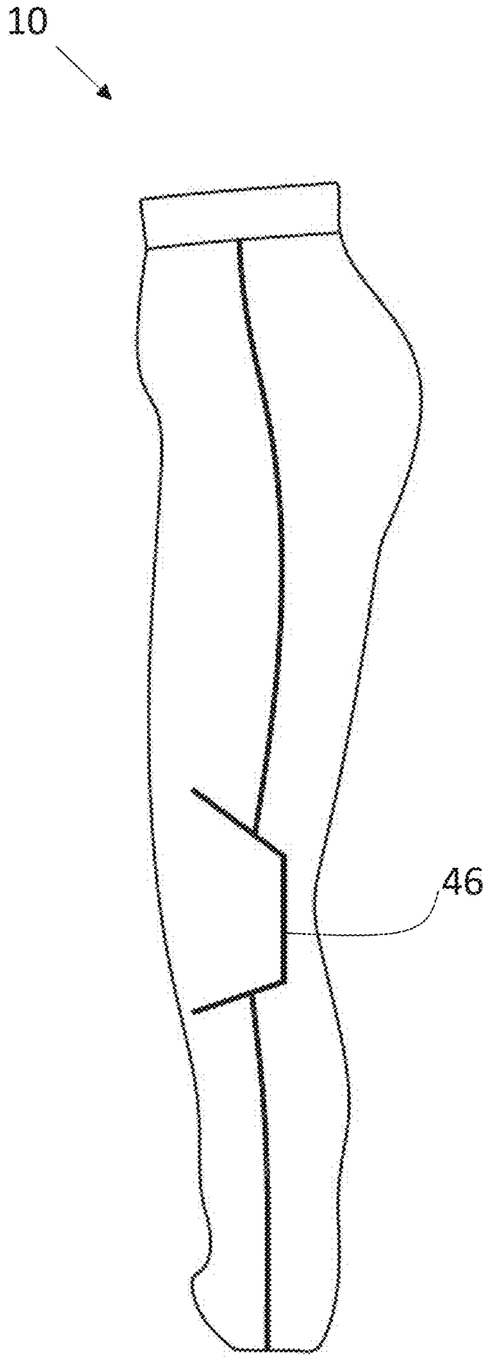
FIG. 7 is a side elevation view of the compression pants for lipedema with a first variation of the pad pocket.
Figure 8:
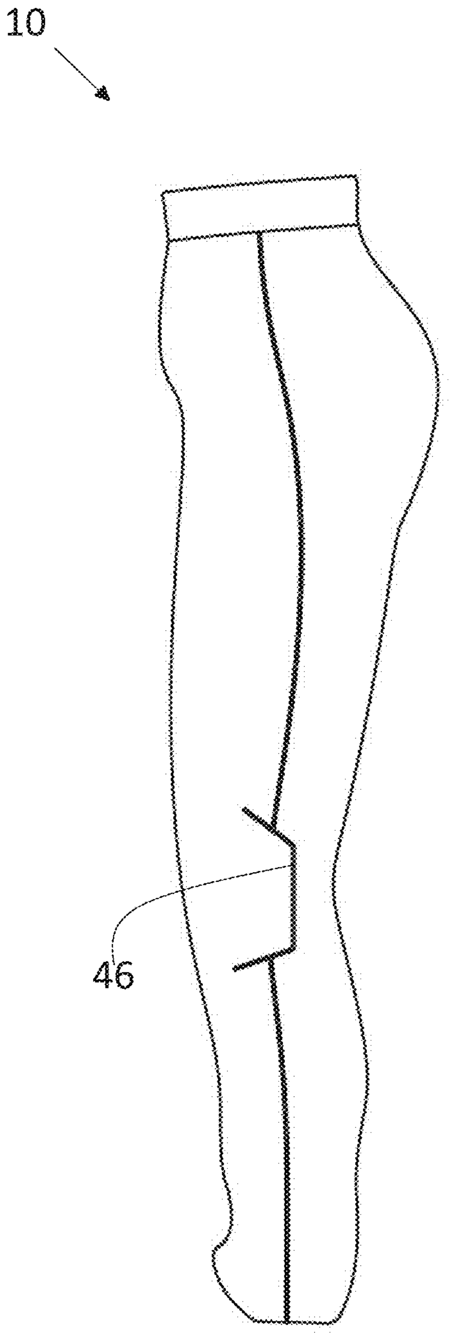
FIG. 8 is a side elevation view of the compression pants for lipedema with a second variation of the pad pocket.
Figure 9:
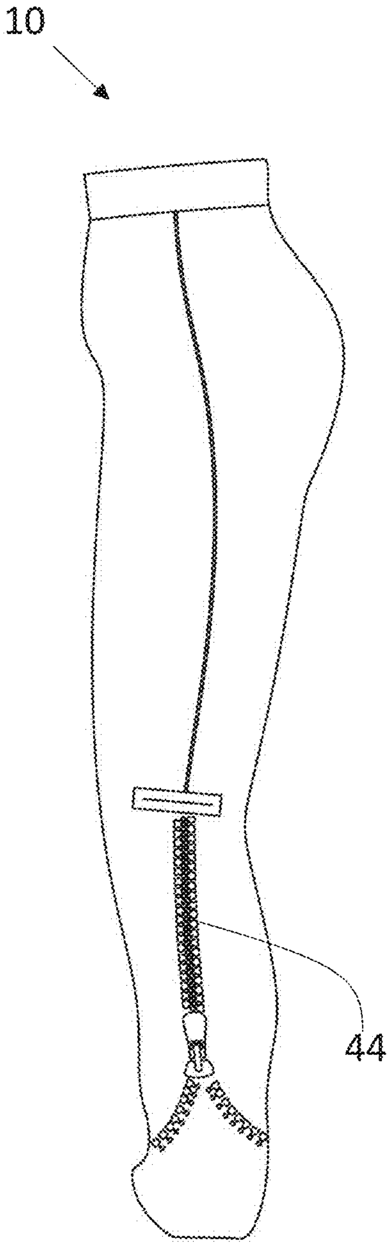
FIG. 9 is a side elevation view of a pad pocket with a zipper.
Figure 10:
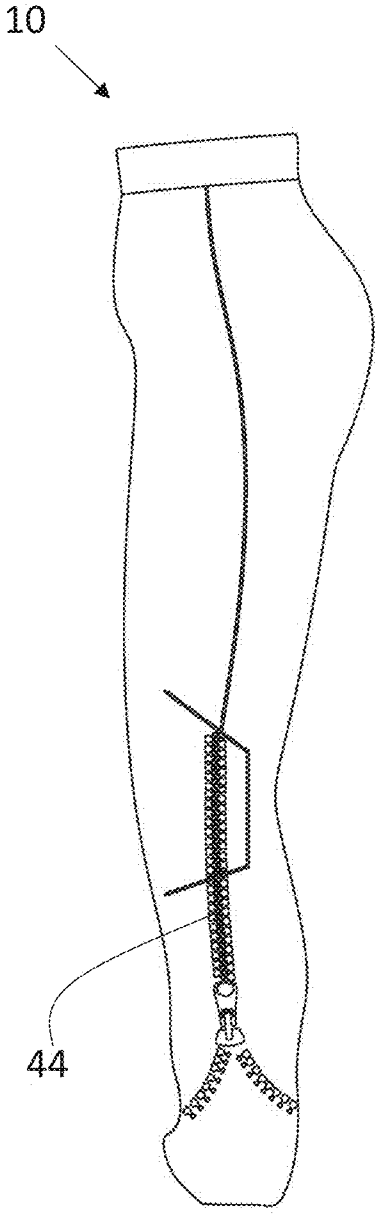
FIG. 10 is a side elevation view of the first variation of the pad pocket with a zipper.
Figure 11:
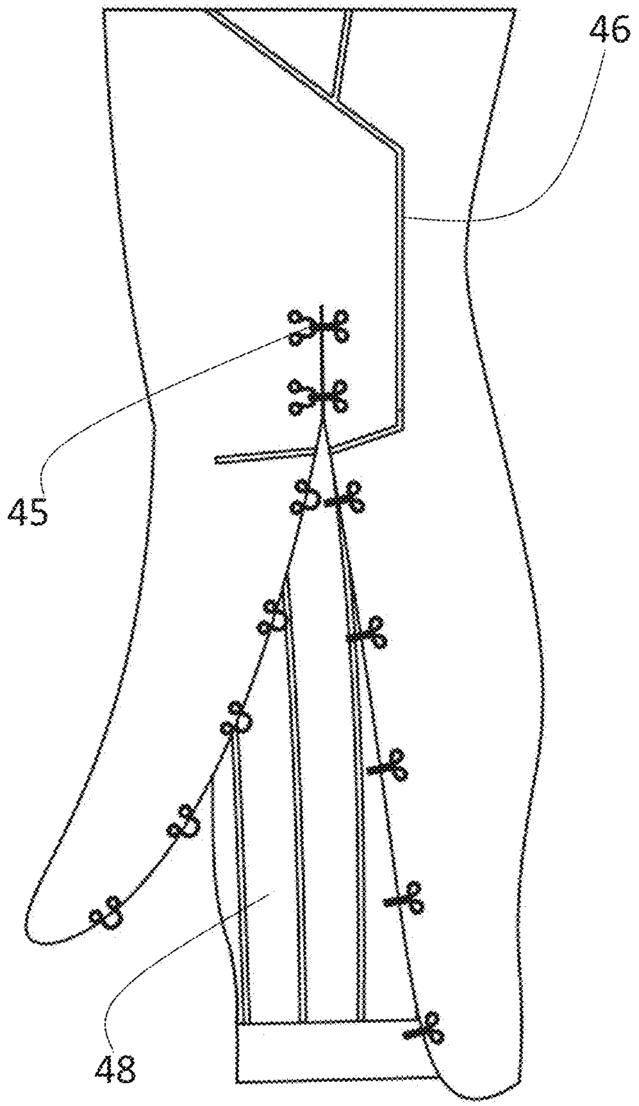
FIG. 11 is a side elevation view of compression pants for lipedema with a removable liner and closure hooks.
Figure 12:
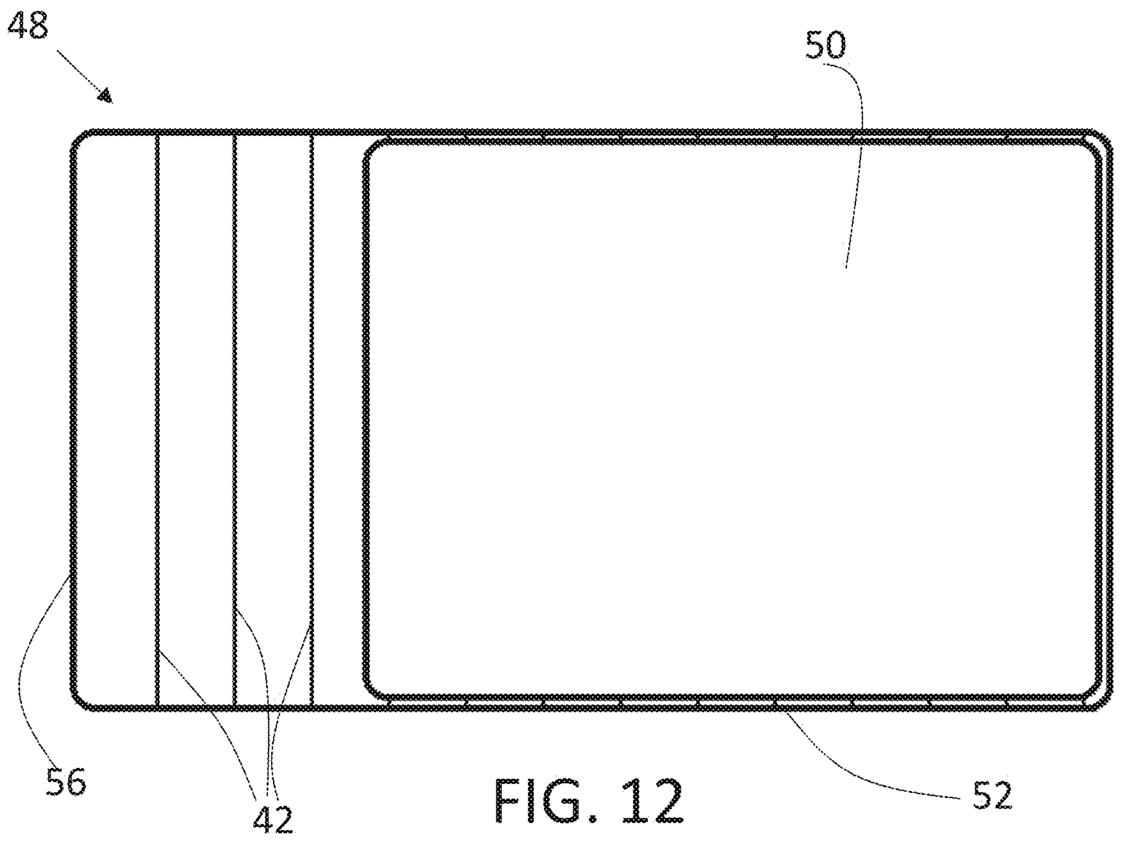
FIG. 12 is a front elevation view of a variation of the removable liner with a foam pad.
Figure 13:
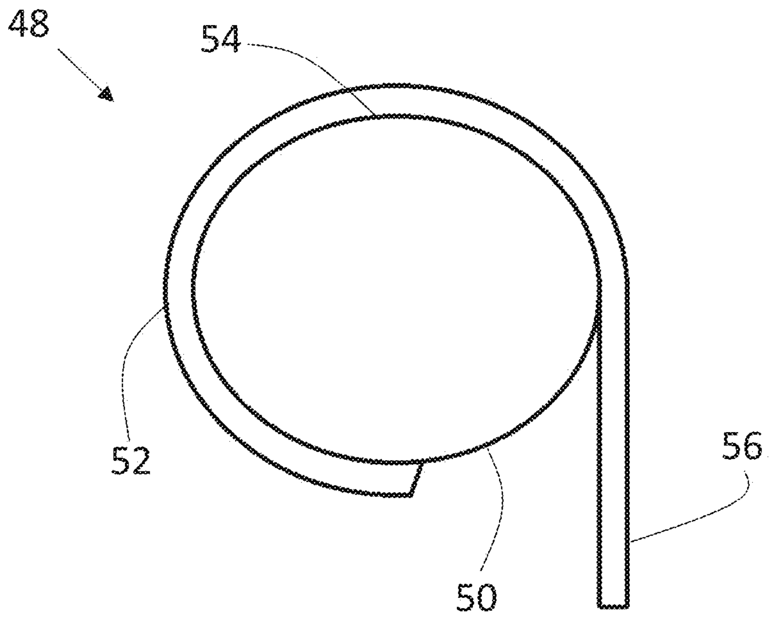
FIG. 13 is a top plan view of the variation of the removable liner with a foam pad.

Referring to FIG. 4, a foam pad 38 may be positioned at a predetermined location of compression pants for lipedema. Foam pad 38 may be positioned to change the pressures applied to an area of the body which may provide additional relief to the wearer and a reduction in fluid accumulation. Predetermined locations may include a side of a knee, back of a knee, a side of the hip, a part of the waist, or anywhere else that a wearer finds beneficial. Foam pad 38 may have a contacting surface 40 that is positioned such that it is adjacent a wearer's body. It will be understood that contacting surface 40 does not need to be in direct contact with the wearer's skin. In the embodiment shown in FIG. 5, contacting surface 40 may have at least one lymph channel 42 that can be positioned to help guide or assist in lymphatic drainage. This can help to reduce excessive swelling in the area of foam pad 38. In the embodiment shown in FIG. 5, foam pad 38 is positioned behind a wearers knee. It will be understood by a person skilled in the art that foam pad 38 may be of any suitable shape, with or without lymph channels 42, and positioned at locations determined by the wearer. In the embodiment shown in FIG. 9 through FIG. 11, a closure in the form of a zipper 44 or hooks 45 is positioned to facilitate the insertion of foam pad 38 into position on a side of a wearer's knee. It will be understood by a person skilled in the art that closure may be positioned in other locations to accommodate insertion of foam pad 38 into other areas. In the present embodiment, zipper 44 extends from the wearer's knee to the ankle and allows for the whole lower leg to be unzipped. However, it will be understood that a smaller zipper 44 could still allow access without unzipping the whole lower leg. It will be understood by a person skilled in the art that other types of closures may be used, including but not limited to Velcro, hooks, snaps, buttons, or ties. Referring to FIG. 6, FIG. 7 and FIG. 8, while foam pad 38, shown in FIG. 4 and FIG. 5, may be held in position by virtue of the compressive nature of compression pants for lipedema 10, a pad pocket 46 may be provided to hold foam pad 38 in position. In the embodiment shown in FIG. 7, pad pocket 46 is a large 3 sided pocket that fully encompasses foam pad 38. In the embodiment shown in FIG. 8, pad pocket 46 is smaller and only partially encompasses foam pad 38. The size of pad pocket 46 may be based on a user's preference. For highly active wearer's, a larger pad pocket 46 that fully encompasses foam pad 38 may be most beneficial, however in other cases, a smaller pad pocket 46 that acts more as a guide for positioning foam pad 38 as opposed to holding foam pad 38 in position may be more beneficial. It will, therefore, be understood by a person skilled in the art that pad pocket 46 may be any size suitable to hold at least a portion of foam pad 38.

As lipedema symptoms worsen, it is possible for suffers to develop lymphorrhea which is a leakage of lymph onto the skin. Lymphorrhea can be extremely uncomfortable for the sufferer and also increases the risk of developing infections in the legs. In addition, lymphorrhea will leave clothing wet and uncomfortable. In the embodiment shown in FIG. 11, a removable liner 48 is provided and positionable between compression pants for lipedema 10 and a wearer's lower leg. A closure, such as a zipper 44, shown in FIG. 9, hooks 45, shown in FIG. 11, or any other suitable closure may also be used to allow a wearer to insert, remove, or replace removable liner 48 as needed. In the embodiment shown in FIG. 12 and FIG. 13, removable liner 48 includes a stretchable fabric front 50 that contacts the wearer's skin. A first portion 52 of foam pad 38 with lymph channels 42 is secured to stretchable fabric front 50 to create a removable liner sleeve 54. A second portion 56 of foam pad 38 with lymph channels 42 extends from first portion 52 and is wrappable around stretchable fabric front 50 such that foam pad 38 with lymph channels 42 circumferentially engages a wearer's lower leg. In the embodiment shown in FIG. 9, removable liner 48 is an absorption liner for collecting fluids. It will be understood by a person skilled in the art that different shapes may be used for removable liner 48 and that removable liner 48 may cover only a portion of a wearer's leg. In a preferred embodiment, removable liner 48 is made of a disposable and absorbent material.

Compression pants for lipedema 10 are made of a stretchable material that can provide between 5-40 mmHg. A person of skill will understand that different types of materials may be used to provide compression and that different types of materials will provide different levels of compression. Nylon, spandex, silicon, cotton, neoprene, lycra, polyamide elastane, polyester, and latex free elastic fabrics may all be used for compression purposes. The amount of compression that is achieved may also be manipulated by choosing between a flat-knit or circular-knit material. It should be noted that compressions pants for lipedema 10 may incorporate more than one type of material and both flat-knit and circular-knit materials in different areas. Compression pants for lipedema 10 are designed to be ready to wear off the shelf. This is beneficial as it can provide wearers with compression garments that are less expensive than custom wear and provide compression garments that can be worn before custom garments are required.

Any use herein of any terms describing an interaction between elements is not meant to limit the interaction to direct interaction between the subject elements, and may also include indirect interaction between the elements such as through secondary or intermediary structure unless specifically stated otherwise.

In this patent document, the word "comprising" is used in its non-limiting sense to mean that items following the word are included, but items not specifically mentioned are not excluded. A reference to an element by the indefinite article "a" does not exclude the possibility that more than one of the element is present, unless the context clearly requires that there be one and only one of the elements.

It will be apparent that changes may be made to the illustrative embodiments, while falling within the scope of the invention. As such, the scope of the following claims should not be limited by the preferred embodiments set forth in the examples and drawings described above, but should be given the broadest interpretation consistent with the description as a whole.

What is claimed is:

1. A compression pants for lipedema, comprising:

a lower waist portion;

a hip portion positioned below the lower waist portion, the hip portion having a circumference significantly larger than the lower waist portion circumference, with a difference of at least 25%;

a right thigh portion and a left thigh portion positioned below the lower waist portion, each thigh portion having an upper part and a lower part, wherein:

each upper part has a circumference 30-45% smaller than the hip portion circumference, each lower part has a circumference 50-60% smaller than the hip portion circumference, the upper part tapers into the lower part; and wherein the combined left and right leg volumes accommodate at least 9,000 mL total leg volume, enabling treatment of lipedema patients without tourniquet effects.

2. The compression pants for lipedema of claim 1 further comprising an upper waist portion positioned above and depending from the lower waist portion.

3. The compression pants for lipedema of claim 1 further comprising a right lower leg portion and a left lower leg portion, the right lower leg portion depending from the lower part of the right thigh portion, the left lower leg portion depending from the lower part of the left thigh portion, each of the right lower leg portion and the left lower leg portion having a knee portion, a calf portion, and an ankle portion, the calf portion being smaller in diameter than the lower part of the right thigh portion and the left thigh portion, the ankle portion being smaller in diameter than the calf portion.

4. The compression pants for lipedema of claim 3 further comprising a foot portion depending from the ankle portion, the foot portion extending from the ankle portion towards a wearer's toes.

5. The compression pants for lipedema of claim 3 wherein the left thigh portion and the left lower leg portion accommodate a combined left leg volume of at least 9000 mL and the right thigh portion and the right lower leg portion accommodate a combined right leg volume of at least 9000 mL.

6. The compression pants for lipedema of claim 3 wherein a removable inner liner is positionable between the compression pants for lipedema and a wearer's lower leg.

7. The compression pants of claim 1, wherein the proportional relationships between hip, upper thigh, and lower thigh are calibrated to address tourniquet effects in lipedema patients while enabling gradient compression therapy.

8. The compression pants for lipedema of claim 1 further comprising a foam pad positioned at a predetermined location of the compression pants for lipedema.

9. The compression pants for lipedema of claim 8 wherein the foam pad has a contacting surface, the contacting surface being positioned such that it is adjacent a wearer's body, the contacting surface having at least one lymph channel.

10. The compression pants for lipedema of claim 8 wherein the predetermined location is a side of the wearer's knees.

11. The compression pants for lipedema of claim 8 wherein the predetermined location is a side of the wearer's hip.

12. The compression pants for lipedema of claim 8 wherein a closure is positioned adjacent the predetermined location to facilitate insertion of the foam pad.

13. The compression pants for lipedema of claim 8 wherein a pad pocket is provided at the predetermined location for holding the foam pad.

14. The compression pants for lipedema of claim 8 wherein the foam pad is held in position through compression of the compression pants for lipedema.

15. The compression pants for lipedema of claim 1 wherein at least a portion of the compression pants for lipedema are flat-knit.

16. The compression pants for lipedema of claim 1 wherein at least a portion of the compression pants for lipedema are circular-knit.

* * * * *